Figure 1:
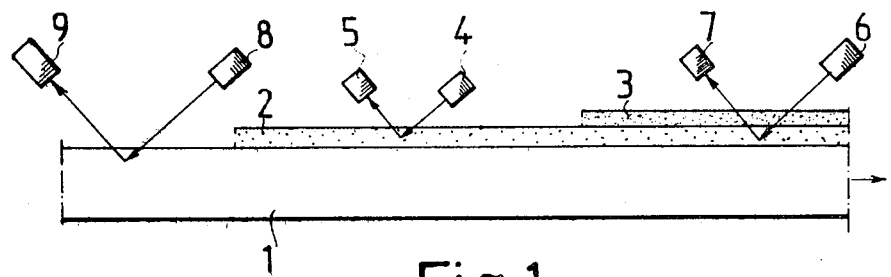

United States Patent [19]

Venalainen et al.

[11] 4,377,869
[45] Mar. 22, 1983

[54] PROCEDURE FOR MEASURING COATING RATES

[75] Inventors: Heikki Venalainen; Rauno Rantanen, both of Imatra; Rertti Puumalainen, Kuopio, all of Finland

[73] Assignee: Enso-Gutzeit Osakeytio, Hesinki, Finland

[21] Appl. No.: 259,496

[22] Filed: May 1, 1981

Related U.S. Application Data

[62] Division of Ser. No. 95,326, Nov. 19, 1979.

[30] Foreign Application Priority Data

Nov. 21, 1978 [FI] Finland .............................. 783544

[51] Int. Cl.³ .......................................... G01N 23/22
[52] U.S. Cl. .................................... 378/50; 378/210
[58] Field of Search ......................................... 378/50

[56] References Cited

U.S. PATENT DOCUMENTS

| | | | |
|---|---|---|---|
| 2,711,480 | 6/1955 | Freedman | 378/50 |
| 3,984,679 | 10/1976 | Lublen | 378/50 |
| 4,129,778 | 12/1978 | Inoue | 378/50 |
| 4,147,931 | 4/1979 | Puumalainen | 378/50 |
| 4,162,528 | 7/1979 | Maldonado | 378/50 |

Primary Examiner—Craig E. Church
Attorney, Agent, or Firm—Toren, McGeady and Stanger

[57] ABSTRACT

The invention concerns a procedure for measurement of the material quantities in coating layers applied upon a base material, by utilizing x-ray radiation. The procedure is particularly suited for use in a paper or cardboard manufacturing process wherein onto a material web in continuous motion are applied by steps one or several coating courses. The radiation source and detector are both placed on one side of the moving web, and the procedure is based on measurement of the fluorescence radiation excited by the primary x-ray radiation obtained from the radiation source in the material underlying the coating layer that is to be measured. The primary and secondary radiation both are thereby compelled to pass through the coating layer under measurement before the arrival of the fluorescence radiation at the detector. The moving web may be equipped with a plurality of consecutive pairs of radiation source and detector, the first pair measuring the fluorescence radiation from the base material before application of the coating layer and the latter measuring the equivalent fluorescence radiation after applying the coating layer, in above-presented manner. It is alternatively possible to use one single radiation source and detector and to measure simultaneously the fluorescence radiation produced both in the coating layer under measurement and in the underlying base material.

3 Claims, 3 Drawing Figures

PROCEDURE FOR MEASURING COATING RATES

This is a division of application Ser. No. 095,326, filed Nov. 19, 1979.

The present invention concerns a procedure for on-line measurement of the coating rate in combinations of materials comprising one or several surface coatings and under these a base material, or a pre-coating upon the base material, capable of emitting isotope or x-ray tube-excited characteristic secondary x-ray radiation.

It is known in prior art, through the Finnish Pat. No. 53757, to measure the base weights of a $CaCO_3$ course applied as pre-coating 2 on cardboard or paper 1 and of the caolin-containing surface coating 3 thereupon by employing x-ray radiation which excites the characteristic secondary x-ray radiation of the Ca in the pre-coating 2 and the intensity of this radiation being measured from over and under the cardboard web by means of detectors 7 and 6, in addition to which the absorption of the primary radiation coming from the source of radiation 4 in the entire materials combination is measured, whereby from the obtained, mutually independent results of measurement the base weights of courses 1, 2 and 3 can be calculated by the principle of three equations with three unknown.

It is also known in the art to measure the coating rate in one coating course on paper by utilizing the characteristic secondary x-ray radiation excited by primary x-ray radiation in a marker substance added to the coating material.

The procedure for measurement of the base weights of coating layers of the Pat. No. 53757 is encumbered by the drawback that the work involved in the calibration of a coating rate meter capable of measuring in on-line conditions two different coating layers is cumbersome because in order to be operative the method requires that several constants difficult to determine are measured before the equations forming the basis of the method can be solved and the different base weights determined. The method is moreover sensitive to variations in the geometry of measurement, since no primary radiation must be allowed to strike the fluorescence detector on the side opposite from the source.

The latter method has the drawback that by this method the coating rate of only one coating layer can be measured and this too only in case the coating layer in question gives rise to secondary x-ray radiation in measurable quantity.

The object of the present invention is to avoid the drawbacks mentioned and to provide a method, of simple operating characteristics and particularly appropriate for measurements on line, for the measuring of the coating material quantities, or coating rates, in one or several coating layers. The invention is in particular intended for use in connection with the manufacturing process of paper, cardboard or another equivalent paper product.

The invention is characterized by that which is stated in the attached claims.

Three different embodiments of the procedure of the invention are schematically presented in the figures, of which FIG. 1 illustrates the case in which upon the cardboard web constituting the base material 1 there is a precoating layer 2, which may for instance consist of $CaCO_3$, and thereupon as surface coating 3 for instance a caolin course. When subsequent to precoating the combination 1,2 is irradiated with a radiation source 4, which may for instance be a 55-Fe radio isotope source, the Ca atom in the precoating 2 is caused to emit its own characteristic secondary x-ray radiation, or fluorescence radiation, the intensity of this radiation being proportional to the amount of material present, or of Ca in this case. When the intensity of Ca fluorescence radiation arriving at the detector is known as a function of varying $CaCO_3$ quantity, the amount of $CaCO_3$ is calculable from the intensity pulses delivered by the detector 5.

The web 1 moves forward to another coating unit, where the surface coating 3 is applied on the web 1. Hereafter, the combination is irradiated once again with radiation from the radiation source 6, whereby the Ca atoms will emit fluorescence radiation which passes through the surface coating layer 3 and is measured by the detector 7 located above the surface coating layer 3. In this event part of the primary and fluorescence radiations is absorbed, according to a certain experimentally determinable function, in the surface coating course, and the number of pulses entering the detector 7 decreases. In evaluation of the decrease in number of pulses one takes into account the ratio of the two pick-ups' efficiencies of measurement, which can be determined while a web is being run that has merely been base-coated. From the pulse reduction found, the surface coating rate can be calculated.

If the base material contains, in significant amount, such fillers which are able to emit a significant amount of measurable secondary x-ray radiation, or if the base material 1 is coated on the other side as well with a coating able to emit measurable secondary radiation, these effects may be accounted for by irradiating the web with a radiation source 8 acting before the coating step and by measuring the secondary x-ray radiation by means of the detector 9. When this has been done, variations of the base material 1 cause no possible sources of error in the measurement of coating rates. In that case the efficiency of measurement of the pick-up monitoring the raw cardboard must also be taken into account.

Figure 2:
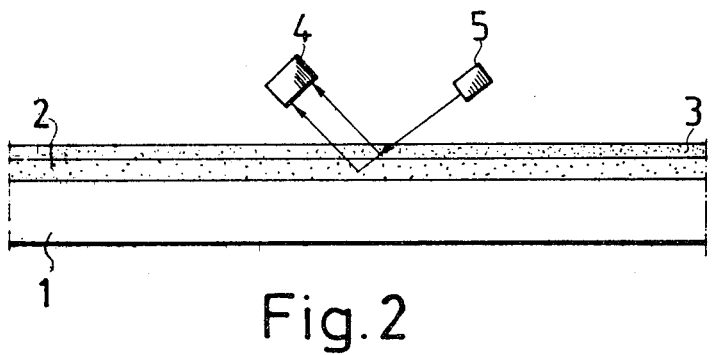

In the case of FIG. 2, there may be upon the base material 1, for instance, a $CaCO_3$ course and thereupon a coating 3 which contains $TiO_2$. It is possible, by irradiating with the source 5 the combination of courses 2 and 3, to measure the coating rates as follows. The quantity of coating layer 3 is a function of the quantity of $TiO_2$ contained in the coating layer 3. If one measures the amount of x-ray radiation with energy 4.5 keV emitted by $TiO_2$, this enables the quantity of the surface coating 3 to be calculated. The primary radiation from the source 5 also excites the Ca in the base coating 2, which emits secondary radiation with energy 3.7 keV. With knowledge of the absorptions of the primary and secondary radiations in the surface coating 3, of which the quantity is already known, one is enabled to calculate which is the quantity of $CaCO_3$ able to cause from under this surface coating 3 the secondary radiation that has been measured. If required, the effect of the raw cardboard may be eliminated by the same procedure as was applied in the exemplary case 1.

Figure 3:
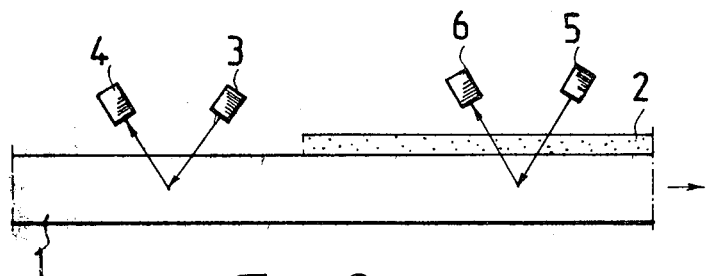

In the case of FIG. 3, the base material 1 contains a substance capable of emitting secondary radiation, either as filler, as background coating or as a material with which the base material has been impregnated. When the base material is irradiated by the source 3 and the secondary radiation is measured with the detector 4, information is gained concerning the secondary radiation emitted by the base material.

As the web moves forward to the coating unit in which the surface coating 2 is applied on the web, the combination is irradiated from the source 5, whereby the atoms in the web will emit fluorescence radiation under influence of the primary radiation that has penetrated through the surface coating 2. The number of pulses received by the detector 6 will then decrease as part of the primary and fluorescence radiations is absorbed in the surface coating course in accordance with a given experimentally determinable function. The coating rate is calculated on the basis of the pulse reduction, taking into consideration the ratio of the two pick-ups' efficiencies of measurement.

The greatest advantage of the present invention lies therein that the sources of error arising from the variations of the uncoated base material have been eliminated therein, thus achieving an exceedingly high accuracy of measurement. In addition, the need of repeating the most cumbersome steps in the calibration procedure is exceedingly little because the ratios of the pick-ups' efficiencies of measurement and the isotope activities may be left to the computer to resolve, the first in fact point by point across the web, whereby the accuracy requirements of the traversing beams may be quite appreciably reduced. The two or three constants which are most cumbersome to determine are mainly dependent on the chemical composition of the coating materials and therefore their need of being redetermined is quite minimal.

We claim:

1. An improvement in a method of determining the quantities of material in a first coating layer applied to cardboard or equivalent base material as well as in a second coating layer applied to said first coating layer, said method comprising the steps of subjecting said first coating layer to a primary X-ray radiation derived from an outside source and travelled via said second coating layer, so as to excite a characteristic fluorescence radiation in said first coating layer, and measuring the intensity of said fluorescence radiation by means of a detector placed above said second coating layer, whereby the determination is based on the absorption of the primary X-ray radiation and the fluorescence radiation while travelling through said second coating layer, the improvement comprising that, in addition to exciting the fluorescence radiation of the first coating layer, the primary X-ray radiation is used to excite a characteristic fluorescence radiation in the second coating layer, which is measured by means of a detector and used as the basis for determination of the quantity of material in the second coating layer, while the measurement of the fluorescence radiation of the first coating layer is performed for the determination of the quantity of material in the first coating layer, with the aid of the quantity of material in the second coating layer as determined.

2. A method according to claim 1, wherein fluorescence radiation is excited in the first and second coating layers simultaneously by using a primary X-ray radiation derived from a single radiation source.

3. A method according to claim 2, wherein the base material is composed of a web of cardboard or paper, which is transported along a line having locations for applying the coating layers and a pair of radiation source and detector for performing the measurements, said pair being placed above said line of transport.

* * * * *